United States Patent
Botzenhart et al.

(10) Patent No.: US 10,842,569 B2
(45) Date of Patent: Nov. 24, 2020

(54) METHOD FOR MANUFACTURING A DISTRACTOR FOR SKELETAL ATTACHMENT TO A JAW

(71) Applicant: Technische Universitat Dresden, Dresden (DE)

(72) Inventors: Ute Ulrike Botzenhart, Dresden (DE); Bernhard Weiland, Dresden (DE); Tomasz Gedrange, Dresden (DE)

(73) Assignee: TECHNISCHE UNIVERSITAT DRESDEN, Dresden (DE)

( * ) Notice: Subject to any disclaimer, the term of this patent is extended or adjusted under 35 U.S.C. 154(b) by 53 days.

(21) Appl. No.: 15/772,499

(22) PCT Filed: Nov. 1, 2016

(86) PCT No.: PCT/DE2016/100514
§ 371 (c)(1),
(2) Date: Apr. 30, 2018

(87) PCT Pub. No.: WO2017/076389
PCT Pub. Date: May 11, 2017

(65) Prior Publication Data
US 2018/0318010 A1    Nov. 8, 2018

(30) Foreign Application Priority Data
Nov. 3, 2015   (DE) .......... 10 2015 118 853

(51) Int. Cl.
*A61B 34/10*   (2016.01)
*A61C 7/00*    (2006.01)
(Continued)

(52) U.S. Cl.
CPC .......... *A61B 34/10* (2016.02); *A61B 17/0218* (2013.01); *A61C 7/002* (2013.01);
(Continued)

(58) Field of Classification Search
CPC ...... A61B 34/10; A61B 17/663; A61B 17/666
See application file for complete search history.

(56) References Cited

U.S. PATENT DOCUMENTS

| | | | | |
|---|---|---|---|---|
| 2011/0059413 | A1* | 3/2011 | Schutyser | A61C 19/05 433/8 |
| 2015/0057675 | A1* | 2/2015 | Akeel | G16H 50/50 606/130 |

FOREIGN PATENT DOCUMENTS

| | | | | |
|---|---|---|---|---|
| EP | 2687168 A1 * | 1/2014 | | A61B 17/8071 |
| WO | 01/80752 A1 | 11/2001 | | |
| WO | WO-0180752 A1 * | 11/2001 | | A61B 17/663 |

OTHER PUBLICATIONS

Ulrike, Botzenhart Ute et al; "Mandibular Midline Distraction Osteogenesis"; Journal "Oral Health and Dental Management"; Department of Orthodontics; Dec. 2017; pp. 305-312; Dresden, Germany.

(Continued)

*Primary Examiner* — Julianna N Harvey
(74) *Attorney, Agent, or Firm* — Brian R. Galvin; Galvin Patent Law LLC

(57) ABSTRACT

The invention related to a method for manufacturing a distractor for skeletal attachment to a jaw of a patient. This method comprises the steps of:
(a) generating a three-dimensional image of the jaw of the patient or of parts of the jaw;
(b) generating a virtual model of a patient-specific distractor using the three-dimensional image; and
(c) manufacturing the distractor or parts thereof with the help of the virtual model.

13 Claims, 3 Drawing Sheets

(51) Int. Cl.
  *A61C 9/00*     (2006.01)
  *A61C 7/10*     (2006.01)
  *B33Y 50/00*    (2015.01)
  *A61B 17/02*    (2006.01)
  *G05B 19/4099*  (2006.01)
  *A61B 17/00*    (2006.01)

(52) U.S. Cl.
  CPC ........... *A61C 7/10* (2013.01); *A61C 9/004* (2013.01); *B33Y 50/00* (2014.12); *G05B 19/4099* (2013.01); *A61B 2017/00526* (2013.01); *A61B 2034/105* (2016.02); *G05B 2219/35134* (2013.01); *G05B 2219/49007* (2013.01)

(56) References Cited

OTHER PUBLICATIONS

"Variety / Variety SP Screw"; Dentaurum GmbH & Co. KG, Ispringen, Germany; Oct. 2014.
Gebrüder Martin GmbH & Co. KG; The Bologna Midline Distractor (BMD); Jul. 2012; pp. 1-8; Tuttlingen, Germany.
Gebrüder Martin GmbH & Co. KG; The Rotterdam Midline Distractor (RMD); Oct. 2012; pp. 1-8; Tuttlingen, Germany.
Harzer, Winfried et al.; Rapid Maxillary Expansion with Palatal Anchorage of the Hyrax Expansion Screw—Pilot Study with Case Presentation; Journal of Orofacial Orthopedics; Jan. 27, 2004; pp. 419-424, No. 5; Urban & Vogel; Dresden, Germany.

* cited by examiner

METHOD FOR MANUFACTURING A DISTRACTOR FOR SKELETAL ATTACHMENT TO A JAW

The invention relates to a method for manufacturing a distractor, especially a lower jaw distractor. Further, it relates to a distractor, especially a lower jaw distractor obtainable with the method according to the invention.

The lower jaw symphysis consists of two paired portions that ossify already very early, i.e. in the first year of life (Becker M J. Mandibular symphysis (medial suture) closure in modern *Homo sapiens*: preliminary evidence from archaeological populations. American journal of physical anthropology 1986; 69: 499-501). Thus, the bony width of the lower jaw can only partly be influenced by conventional orthodontic measures. In case of distinct lack of space symphyseal distraction represents an alternative method for extraction therapy of permanent teeth for the purpose of creating space. The method described by Guerrero et al. in 1997 for the first time is a still relatively new method compared to other surgical methods (Guerrero C A, Bell W H, Contasti G I et al. Mandibular widening by intraoral distraction osteogenesis. The British journal of oral & maxillofacial surgery 1997; 35: 383-392). Among the known distractors a basic distinction is made between tooth-borne, dental, and bone-borne, skeletal distractors. Dental distractors are described for example in DE 197 12 791 A1, DE 102 13 823 A1 and EP 1 088 520 A2. Skeletal distractors are described for example in U.S. Pat. No. 6,302,687 B2 and DE 601 04 297 T2.

Since with dentally supported distractors undesirable tooth movements can occur (Seeberger R, Kater W, Davids R et al. Changes in the mandibular and dento-alveolar structures by the use of tooth borne mandibular symphyseal distraction devices. Journal of cranio-maxillo-facial surgery: official publication of the European Association for Cranio-Maxillo-Facial Surgery 2011; 39: 177-181) increasingly skeletally supported distractors are preferred that are laterally fixed on both sides of the lower jaw symphysis and have a transgingival portion with an activator screw in the area of the vestibule.

The shape of the lower jaw symphysis and the lower jaw corpus depends on a high interindividual variability (Jung S Y, Shin S Y, Lee K H et al. Analysis of mandibular structure using 3D facial computed tomography. Otolaryngology-head and neck surgery: official journal of American Academy of Otolaryngology-Head and Neck Surgery 2014; 151: 760-764). As a result, all prefabricated systems have to be adapted, i.e. prebend by the surgeon during the operation. On the one hand, this results in an increased inaccuracy of the fitting and unpredictability of the subsequently acting force vectors that are correlated with the variance of placement and accuracy in fitting (Basciftci F A, Korkmaz H H, Iseri H et al. Biomechanical evaluation of mandibular midline distraction osteogenesis by using the finite element method. American journal of orthodontics and dentofacial orthopedics: official publication of the American Association of Orthodontists, its constituent societies, and the American Board of Orthodontics 2004; 125: 706-715). On the other hand, the transition region between the skeletal fixation option and the transgingival portion with screw has an increased disposition to fracture and the epigingival portion is often very voluminous, respectively and especially in case of a flat duplicature can contribute to irritation of the soft tissues and inflammation. Further, with prefabricated systems an increased operating time is to be expected due to the need of adaption.

Adaption of the prefabricated conventional systems by the surgeon to the individual circumstances of each patient can already take place pre-surgically on a model of the lower jaw, for example a stereo lithography model or a 3D printed model. However, a certain inaccuracy of fitting must always be compensated during the operation. Moreover, material weakening by torsion and bending cannot be avoided. That is, at present there are no satisfying solutions for the above-mentioned problems.

Thus, additionally to disadvantages of a dentally supported distractor there are disadvantages of the skeletal distractor. Dentally supported distractors are associated with undesirable tooth movements and tooth tiltings due to the action of forces (Seeberger et al, loc. cit.); a stenosis of the lingual cavity; an increased risk of caries; a more difficult access for the surgeon, since insertion takes place pre-surgically; and the risk of loosening, namely during the operation or during the consolidation phase and a difficult re-positioning (Alkan A, Ozer M, Bas B et al. Mandibular symphyseal distraction osteogenesis: review of three techniques. International journal of oral and maxillofacial surgery 2007; 36: 111-117). Skeletally supported distractors only provide a relative inaccuracy of fitting; require adaption during the operation; there is a variance in the positioning; there is the risk of damaging dental root; the force vectors are relatively unpredictable, especially a too much caudal placement leads to a small opening of the distraction gap in the dental arc; there is disposition to fracture (Uckan S, Veziroglu F, Arman A. Unexpected breakage of mandibular midline distraction device: case report. Oral surgery, oral medicine, oral pathology, oral radiology, and endodontics 2006; 102: e21-25); irritation of soft tissues by voluminous portion in the vestibule can occur; operating time can be prolonged due to the need of adaption; and finally exposition of the mental foramen for location finding is required what may entail the risk of a damage of the mental nerve and its branches (Apostolakis D, Brown J E. The dimensions of the mandibular incisive canal and its spatial relationship to various anatomical landmarks of the mandible: a study using cone beam computed tomography. The International journal of oral & maxillofacial implants 2013; 28: 117-124; Miller R J, Edwards W C, Boudet C et al. Maxillofacial anatomy: the mandibular symphysis. The Journal of oral implantology 2011; 37: 745-753; Pires C A, Bissada N F, Becker J J et al. Mandibular incisive canal: cone beam computed tomography. Clinical implant dentistry and related research 2012; 14: 67-73).

It is the object of the invention to eliminate the drawbacks according to the prior art. In particular, a method for manufacturing a jaw distractor is provided that allows to achieve an improved accuracy of fitting of the jaw distractor, to reduce the time needed to adapt the lower jaw distractor to the lower jaw of a patient, and to eliminate the variance in placement of the lower jaw distractor. Further, a jaw distractor is provided that can be manufactured by means of the method according to the invention.

This problem is solved by the features of claims 1 and 14. Suitable developments of the inventions result from the features of the sub-claims.

According to the invention a method for manufacturing a distractor for skeletal attachment to a jaw of a patient is provided, comprising the steps of:
(a) generating a three-dimensional image of the jaw of the patient or of parts of the jaw;
(b) generating a virtual model of a patient-specific distractor using the three-dimensional image; and (c) manufacturing the distractor or parts thereof with the help of the virtual model.

The method according to the invention is particularly suitable for the manufacture of a distractor for skeletal attachment to the lower jaw, especially to the front lower jaw of the patient. However, the method according to the invention is also suitable for the manufacture of a distractor for skeletal attachment to the upper jaw of a patient. In principle, with the method according to the invention an individual distractor for any portion of the jaw or visceral cranium can be generated. Thus, the method according to the invention can also be suitable for the manufacture of a distractor for skeletal attachment to another bone of the face. The method according to the invention can also be adapted to other regions of the body.

It is basically required to keep the exposure to radiation of the patient as low as possible. Thus, it may be sufficient to generate a three-dimensional image of only a part of the jaw. This especially applies if a three-dimensional image of only a part of the jaw is sufficient to manufacture a patient-specific distractor. For linguistic simplification the invention is explained below with the help of a three-dimensional image of the jaw. However, the invention can also be practiced with a three-dimensional image of only a part of the jaw.

The three-dimensional image can be generated by a radiographic method or other 3D image-generating techniques. For example, the three-dimensional image can be generated by means of imaging methods such as computer tomography, magnetic resonance tomography, or dental volume tomography. Typically, in these methods at first several two-dimensional images are obtained. These images can be assembled to a three-dimensional image by means of a data processing device, for example a computer. The three-dimensional image can be provided as volume rendering, for example a volume rendering assembled of voxels. From such a volume rendering in turn three-dimensional views of the jaw can be generated. The term "three-dimensional image", as used in the present invention, denotes both the images intermediately obtained by means of the imaging methods and the illustrations of the jaw calculated therefrom, provided that the data allow a three-dimensional illustration of the jaw. A three-dimensional image can enable a 3D illustration of the jaw.

The three-dimensional image can be provided as a medical data record. Such a medical data record is also referred to as a medical 3D data record. The medical data record now suitably contains only data that are required to form a virtual model of the distractor in step (b) of the method according to the invention. The medical data record may be the basis for a virtual model of the jaw. However, alternatively or additionally, it is also possible to directly employ the three-dimensional image, i.e. without previous generation of a medical data record, to form the virtual model of the distractor.

Regardless of whether a medical data record or directly a three-dimensional image of the jaw is employed to generate a virtual model of the patient-specific distractor it may be provided that a virtual model of the jaw is formed first. Then, the virtual model of the patient's jaw can be used to form the virtual model of the patient-specific distractor. The virtual model of the jaw can be formed from the medical data record or the three-dimensional image using mathematical methods. For carrying out such a mathematical method a data processing device, for example a computer, can be used. The virtual model can be provided as a 3D-CAD data record.

It may be provided that the three-dimensional image, the medical data record obtained therefrom, or the virtual model of the jaw are used to determine reference structures of the jaw. Reference structures are for example anatomic features of the jaw that are patient-specific. Such reference structures are for example the position of the mental foramina, the course of the nerve canals as well as dental structures. The position of the reference structures can be used to adapt the virtual model of the distractor to the patient-specific peculiarities of the jaw. By means of the reference structures it can for example be ensured that anchorages for attachment of the patient-specific distractor to the jaw of the patient need not be made in areas of the jaw that are unsuitable or unfavorable from the medical point of view. For example, such areas are areas into which the nerve canals extend or end, for example the mental foramina. In this way, damages of the nerves when attaching the distractor can be prevented. On the other hand, certain reference structures can be used to determine areas of the jaw that from a medical point of view are particularly suitable to receive anchorages of the distractor. The reference structures can be used to generate a virtual model of the patient-specific distractor that is exactly adapted to the anatomic peculiarities of the patient.

The virtual model of the distractor allows an adaption to the patient-specific peculiarities. Thus, it reduces the time associated with an adaption of conventional distractors during the operation. For manufacturing the distractor according to the invention it is possible to illustrate reference features and/or other anatomic features, for example nerve canals or the mental foramina in the three-dimensional image. The same applies to the medical data record obtained from the three-dimensional image or the virtual model of the jaw. In particular, the method according to the invention enables to determine the anchorages for attachment of the patient-specific distractor specifically for each patient.

According to invention it is provided in step (c) that the patient-specific distractor or parts thereof are manufactured with the help of the virtual model. Preferably, here a procedure is employed that enables a fast production of the distractor. A preferred procedure is the 3D printing, more preferably the 3D metal printing and especially preferred the 3D titanium printing. In the 3D titanium printing titanium is employed as the raw material. It is not required to manufacture the entire distractor with the help of the virtual model to achieve a complete adaption of the distractor to the patient-specific features of the jaw, especially its anatomic peculiarities. However, preferably the entire patient-specific distractor is manufactured with the help of the virtual model.

Not all parts of the distractor necessarily need a patient-specific adaption. This especially applies to the parts of the distractor that are not directly attached to the jaw of the patient. Parts of the distractor that are directly attached to the jaw of the patient form the skeletal portion of the distractor. Parts of the distractor that are attached to the jaw via other parts of the distractor form the non-skeletal portion of the distractor. It may be provided that only the skeletal portion of the distractor is manufactured with the help of the virtual model, while the non-skeletal portion consists of prefabricated elements. For example, the distraction cylinder with which the distance between the two fixing arms can be changed can be a standard, i.e. prefabricated element. On the other hand, the fixing arms that are attached to the jaw must be completely adapted. It may therefore be sufficient to only manufacture the fixing arms with the help of the virtual model and to use standard elements for the other parts of the distractor. It may also be provided to manufacture the fixing arms and the connecting elements required to attach the fixing arms to the jaw with the help of the virtual model and to use standard elements for the other parts of the distractor. The connecting elements may be screws or first plug-in connecting elements that can be screwed or plugged into holes created in the jaw at the anchorages. Thus, the skeletal portion of the distractor comprises the fixing arms. Further, it can also comprise the connecting elements. The non-skeletal portion of the distractor comprises the distraction cylinder. If the connecting elements are not assigned to the skeletal portion it can comprise the connecting elements. Further, it can comprise all the additional parts of the distractor, for example guide pins. The assignment of the connecting elements to the skeletal portion or to the non-skeletal portion can be made by a physician, especially by a dentist.

Second plug-in connections may be provided when connecting a prefabricated component, e.g. a prefabricated screw, to a patient-specific part of the distractor. Then, the second plug-in connection is not disposed between the distractor and the jaw, but between the prefabricated and the patient-specific component.

The method according to the invention can be carried out by means of a device that has a unit for generating the three-dimensional image; a data processing unit for creating the virtual model of the patient-specific distractor as well as a unit for manufacturing the patient-specific distractor or parts thereof. The unit for generating the three-dimensional image can be an X-ray apparatus, for example a dental volume tomograph or a computer tomograph. The data processing unit for creating the virtual model of the patient-specific distractor can be a computer. The data processing unit can have and perform a software or software module with which the virtual model of the patient-specific distractor can be generated. The unit for manufacturing the patient-specific distractor can be a 3D printer. The device can have communication means, for example cables to transfer data between the units. The data processing unit can have and perform a software or software module that is suitable to control the unit for generating the three-dimensional image, the unit for manufacturing the patient-specific distractor or both units. Further, the data processing unit can have and perform a software or software module with which a virtual model of the jaw or a part thereof is generated. It can further have and perform a software or software module with which a medical data record is generated from the three-dimensional image. The method according to the invention for manufacturing a distractor can be a purely digitally controlled method.

According to the invention there is further provided a distractor for skeletal attachment to a jaw or another bone of the face of a patient. The distractor is manufactured by means of the method according to the invention, so that it is exactly adapted to the jaw or the other bone of the face of the patient. Thus, the distractor according to the invention is a patient-specific distractor that is exactly adapted to the anatomic circumstances of the patient. The method according to the invention allows the manufacture of a distractor taking into account the anatomic variability of the features of patient jaws. Thus, a distractor can be obtained that requires only little time for attachment to the jaw or another bone of the face of the patient. Due to the exact adaption of the distractor according to the invention to the anatomic features of the patient moreover, the chances of recovery of the patient are improved. In particular, the rate of complications decreases. Unexpected side effects, comparable to conventional distractors, are not to be expected.

Thus, the method according to the invention and the distractor according to the invention enable an exact and clear placement of the distractor on the jaw during the operation. In this way, the operation time and operation risk decrease. Accordingly, the surgical access can be chosen minimally invasive. Exposition of the mental nerve can be avoided. The risk of damages of the dental root is reduced. Force vectors can be preoperatively determined, for example with the help of the three-dimensional image or the virtual model of the distractor. The method according to the invention and the distractor according to the invention enable a complete individualization of the distractor with an exact adaptation to the symphyseal region of the jaw during the operation, especially of the lower jaw. The method according to the invention enables the manufacture of a distractor also taking into account the biomechanical components and surgical components, especially the type of incision, in addition to the anatomic structures. The distractor according to the invention can be placed on the jawbone. It is not implanted into the jawbone. The distractor according to the invention is intended for temporal use. It is particularly suitable for transverse distension of the lower jaw.

The placement of the distractor according to the invention is possible without any tools. The distractor according to the invention due to its high accuracy of fitting may be self-placing. The manufacture of transfer aids and manufacture of a stereo lithography model are omitted. Also, manufacture of a positive-negative mold is not required. The method according to the invention can provide the use of a medical 3D data record, a 3D construction of a virtual model and a 3D implementation of the virtual model in the distractor according to the invention.

Although the invention has been described above in connection with a jaw, so it can readily also be applied to other bones of the face.

In the following, the invention is explained in detail with the help of examples not intended to limit the invention with respect to the drawings. Here, FIG. 1 shows an illustration of three-dimensional print-outs of the lower jaw of patients (FIG. 1a: lower jaw of a first patient; FIG. 1b: lower jaw of a second patient);

Figure 1A:
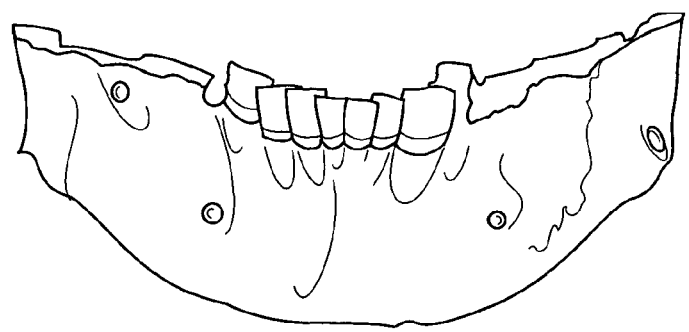
Figure 1B:
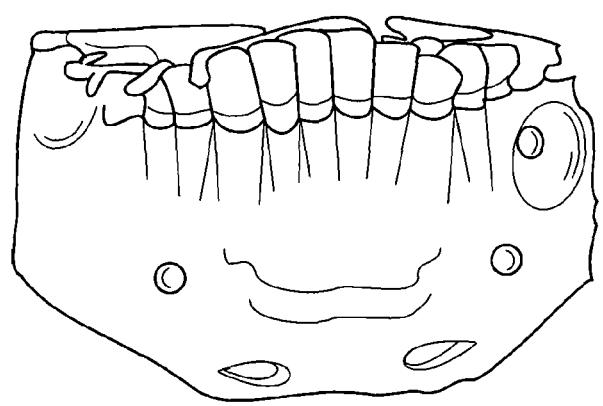

FIG. 1 shows three-dimensional print-outs of the lower jaws of two patients. Such print-outs can be made by generating three-dimensional images of the lower jaws of patients by means of three-dimensional X-ray diagnosis, for example dental volume tomography, generating virtual models of the lower jaws with the help of said images, and subsequently using the virtual models of the lower jaws to print out models of the lower jaws. FIGS. 1a and 1b illustrate the high interindividual anatomic variability of the lower jaw. It should be noted that it is not required to fabricate three-dimensional print-outs for carrying out the method according to the invention and for manufacturing the distractor according to the invention. There is used a virtual model of the lower jaw.

Figure 2:
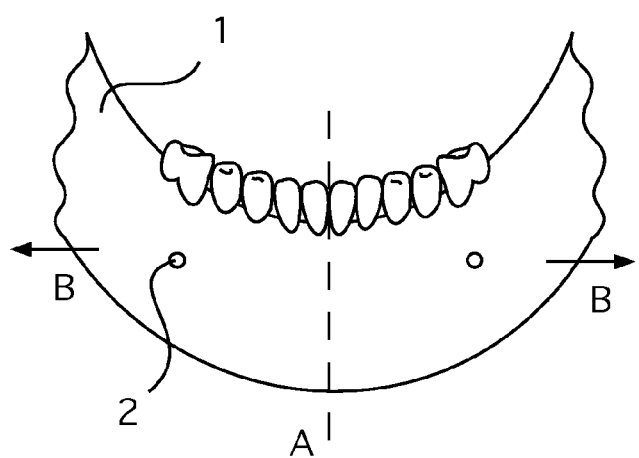
FIG. 2 shows a schematic front view of the lower jaw of a patient.

In FIG. 2, a schematic illustration of the patient's front lower jaw 1 is shown. In the illustration, the mental foramina 2 are shown that are an anatomic feature the position of which varies from patient to patient. Thus, the mental foramina 2 represent one of the anatomic peculiarities that have to be taken into account in the manufacturing of the distractor according to the invention. Thus, they may serve as reference structures. Line A in FIG. 2 indicates the type of incision in a vertical osteotomy of the lower jaw. By means of the distractor according to the invention the parts of the lower jaw separated at line A are to be moved away from each other in the direction of arrows B.

Figure 3A:
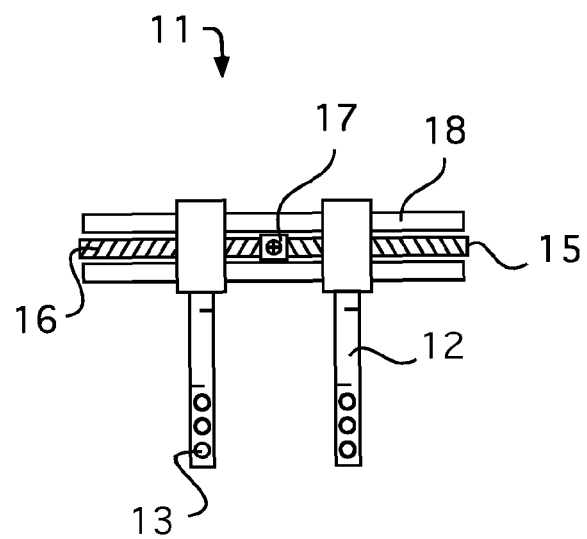
FIG. 3 shows a schematic illustration of an embodiment of a distractor according to the invention to widen the front lower jaw of a patient (FIG. 3a: plan view.
FIG. 3b: side view).
Figure 3B:
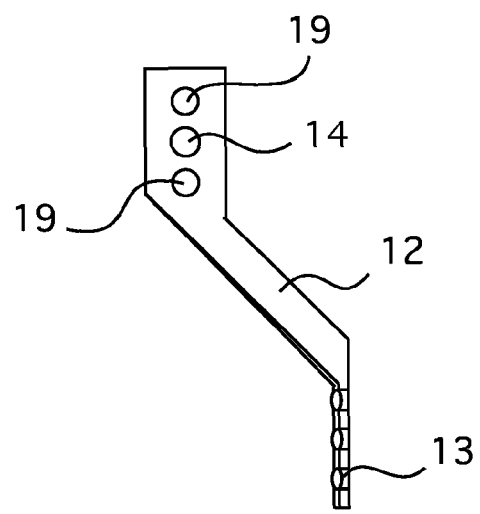

In FIGS. 3a and 3b an embodiment of a distractor 11 according to the invention is shown. It should be noted that the method according to the invention and the distractor according to the invention are not limited to said embodiment, but are directed to any distractor that is adapted to the anatomic peculiarities of the patient and thus, is a patient-specific distractor. The embodiment of the distractor 11 according to the invention shown in FIGS. 3a and 3b has two fixing arms 12 to be attached to the lower jaw of the patient. In the fixing arms 12 first openings 13 are formed through which screws can be passed to attach the fixing arms 12 to the lower jaw 1. The method according to the invention enables to manufacture a distractor 11 that is adapted to the specific anatomic circumstances of the lower jaw of a patient. So, position, number, and orientation of the first openings can be selected such that the anchorages on which holes are formed in the jaw 1 to receive screws have an optimum position to achieve the aim of the treatment—widening the front lower jaw 1. The distractor shown in FIGS. 3a and 3b further has second openings 14 in the fixing arms 12 through which a distraction cylinder 15 is passed. The distraction cylinder 15 has male threads 16 capable of engaging with female threads formed in the second openings 14. By means of an adjusting element 17 the distraction cylinder 15 can be rotated to be able to change the distance between the two fixing arms 12. Further, guide pins 18 are provided that are passed through third openings 19 in the fixing arms 12.

It can be seen in FIGS. 3a and 3b in connection with FIG. 1 that length and width of the fixing arms 11 and the position of the first and second openings 13, 14 should be adapted to the anatomic peculiarities of the lower jaw 1 of the patient to be treated to achieve an optimum treatment result, to facilitate the attachment of the distractor 11 to the lower jaw 1, to reduce the time required for that, and to prevent impairment of the patient, for example by placing the screws in the area of the nerve canals. Thus, the method according to the invention provides first to generate a three-dimensional image of the lower jaw 1 of the patient, preferably by means of three-dimensional X-ray diagnosis, to generate a virtual model of a distractor 11 on the basis of the three-dimensional image that is adapted to the anatomic peculiarities of the lower jaw 1, and finally to transfer the virtual model of the distractor 11 into a real distractor 11 that can preferably be manufactured by means of 3D titanium printing. The thus obtained distractor 11 is adapted to the individual circumstances of the patient and thus, completely individualized.

It may be provided that only the two fixing arms 12 and the screws for attaching the fixing arms 12, i.e. the skeletal portion of the distractor 11, are manufactured by means of 3D titanium printing with the help of the virtual model, while standard elements prefabricated from titanium are used for the distraction cylinder 15 and the guide pins, i.e. the non-skeletal portion of the distractor 11. In this way, there is obtained is a completely individualized distractor, i.e. adapted to the anatomic peculiarities of the patient.

LIST OF REFERENCE SYMBOLS 1 lower jaw
2 mental foramen
11 distractor
12 fixing arm
13 first opening
14 second openings
15 distraction cylinder
16 thread
17 adjusting element
18 guide pin
19 third opening

The invention claimed is:

1. A method for manufacturing a patient-specific distractor for skeletal attachment to a lower jaw of a patient, wherein the distractor is exactly adapted to the anatomic features of the patient, comprising the steps of:
generating a three-dimensional image of the lower jaw of the patient or of parts of the lower jaw;
determining reference structures of the lower jaw or a part thereof, wherein the reference structures are used to determine areas of the jaw that are suitable to receive anchorages of the distractor and wherein one of the reference structures is the mental foramen;
generating a virtual model of a patient-specific distractor using the three-dimensional image; and
manufacturing the distractor or parts thereof with the help of the virtual model by means of 3D printing.

2. The method of claim 1, wherein the three-dimensional image is generated by means of an X-ray method.

3. The method of claim 1, wherein the three-dimensional image is generated by means of computer tomography, magnetic resonance tomography, dental volume tomography, or other 3D image-generating techniques.

4. The method of claim 1, wherein the three-dimensional image is provided as a medical data record.

5. The method of claim 1 wherein a virtual model of the lower jaw of the patient or a part of the lower jaw is generated.

6. The method of claim 1, wherein the reference structures of the lower jaw or a part thereof are determined with the help of the three-dimensional image.

7. The method of claim 6, wherein additional reference structures are selected from the group comprising nerve canals and dental structures.

8. The method of claim 1, wherein anchorages for attaching the distractor to the lower jaw of the patient are determined with the help of the three-dimensional image.

9. The method of claim 1, wherein at least parts of the distractor that are to be directly contacted with the lower jaw are manufactured with the help of the virtual model.

10. The method of claim 1, wherein the distractor has fixing arms for attachment to the lower jaw of the patient, connecting elements for attaching the fixing arms to the lower jaw of the patient, and a distraction cylinder for changing the distance between the fixing arms, wherein only the fixing arms or only the fixing arms and the connecting elements are manufactured with the help of the virtual model.

11. The method of claim 1, wherein the distractor or parts thereof are manufactured with the help of the virtual model by means of 3D titanium printing.

12. The method of claim 1, characterized in that the reference structures of the lower jaw or a part thereof are determined with the help of a medical data record.

13. The method of claim 1, characterized in that the reference structures of the lower jaw or a part thereof are determined with the help of a virtual model of the lower jaw.

* * * * *